United States Patent [19]

Hörlein et al.

[11] 4,153,702

[45] May 8, 1979

[54] BASICALLY ALKYLATED DITHIOSALICYCLIC ACID AMIDES AND THEIR USE AS MEDICAMENTS

[75] Inventors: Ulrich Hörlein, Wuppertal; Horst Böshagen, Haan; Friedel Seuter, Velbert, all of Fed. Rep. of Germany

[73] Assignee: Bayer Aktiengesellschaft, Leverkusen, Fed. Rep. of Germany

[21] Appl. No.: 853,710

[22] Filed: Nov. 21, 1977

[30] Foreign Application Priority Data

Dec. 11, 1976 [DE] Fed. Rep. of Germany ....... 2656227

[51] Int. Cl.² ................ C07D 295/12; A61K 31/445
[52] U.S. Cl. ................................... 424/267; 424/244; 424/274; 260/239 A; 260/239 BF; 260/326.25; 546/190
[58] Field of Search ............... 260/293.64, 326.25, 260/239 A, 239 BF; 424/244, 267, 274

[56] References Cited

PUBLICATIONS

Ponci et al., "Chem. Abstracts", vol. 61, (1964), pp. 6299–6300.

*Primary Examiner*—Natalie Trousof
*Assistant Examiner*—R. W. Ramsuer
*Attorney, Agent, or Firm*—Sprung, Felfe, Horn, Lynch & Kramer

[57] ABSTRACT

The invention provides novel antithrombotics diphenyl-disulphide-2,2'-bis-carboxylic acid amides of the general formula

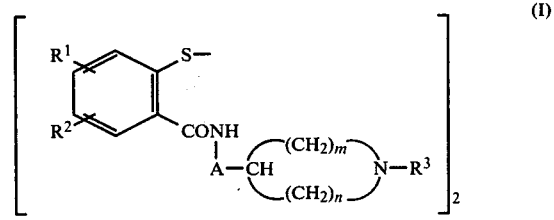

in which
$R^1$ represents a hydrogen or halogen atom or an optionally substituted alkyl, alkoxy or aralkoxy group,
$R^2$ represents a hydrogen or halogen atom or an optionally substituted alkyl or alkoxy group, or together with $R^1$, and adjacent carbon atoms of the benzenoid nucleus, forms an optionally substituted aliphatic or carbocyclic aromatic ring,
$R^3$ represents an optionally substituted alkyl group,
A represents a single bond or an optionally substituted alkylene chain and
m and n each represents 0 or a number from 1 to 5, m and n together having a value of 2-5, and acid addition salts thereof.

Also included in the invention are compositions containing said antithrombotic compounds and methods for using said compounds or compositions for combating thrombo-embolic illness. In addition, the invention includes methods for the preparation of the antithrombotic compounds.

10 Claims, No Drawings

BASICALLY ALKYLATED DITHIOSALICYCLIC ACID AMIDES AND THEIR USE AS MEDICAMENTS

The present invention relates to new basically alkylated diphenyl disulphide-2,2'-bis-carboxylic acid amides, several processes for their preparation and their use as medicaments, in particular as antithrombotics.

Dithiosalicyclic acid amides which carry basic alkyl groups on the amide nitrogen atoms have already been described. For example, F. Gialdi and co-workers, Il Farmaco, Ed. Sci. 16, 411 (1961), report a minimum effect of such substances against fungi. The same amides are protected, in U.S. Pat. No. 3,574,858, as weak bactericides in paper production. Further basically alkylated dithiosalicyclic acid amides are briefly mentioned as intermediate products, without statements on their action, in German Pat. No. 1,147,947 and in the publication of R. Fischer and H. Hurni, Arzneimittelforsch. 14, 1,301 (1964). Basically substituted dithiosalicylic acid amides in which the amide nitrogen atom is one N atom and the baisc group in the other N-atom of 2-aminopyridine or of a piperazine ring are mentioned, inter alia, in DOS (German Published Specification) No. 2,310,572, as a hypoglycaemic agent. The basic group can also be formed by an azacarbocyclic aromatic radical, whilst the amide nitrogen atom is a constituent of an alicyclic ring.

The present invention provides diphenyl disulphide-2,2'-bis-carboxylic acid amides of the general formula (I)

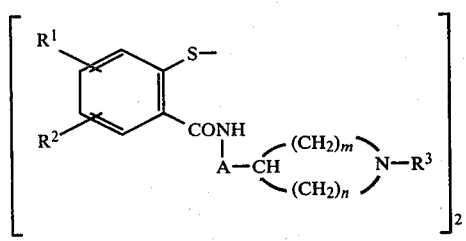
(I)

in which:
$R^1$ represents a hydrogen or halogen atom or an optionally substituted alkyl, alkoxy or aralkoxy group, $R^2$ represents a hydrogen or halogen atom or an optionally substituted alkyl or alkoxy group, or, together with $R^1$, and adjacent carbon atoms on the benzenoid nucleus, forman an optionally substituted aliphatic or carbocycling ring, $R^3$ represents an optionally substituted alkyl group, A represents a single bond or an optionally substituted alkylene chain and m and n each represents O or a number from thrombolic 1 to 5, m and n together having a value of 2–5, and acid addition salts thereof.

The compounds of the invention (ie the compounds of the formula I and their acid addition salts) exhibit an antithromotic effect. Consequently, of those compounds which are salts, the pharmaceutically tolerable salts are most important and preferred.

The diphenyl disulphide -2,2'-bis-carboxylic acid amides of the formula (I) are obtained when (a) diphenyl disulphide-dicarboxylic acid halides of the general formula (II)

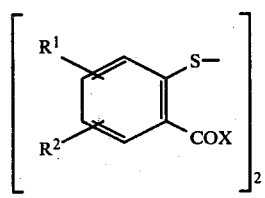
(II)

in which
$R^1$ and $R^2$ have the meaning indicated and
X denotes a halogen atom, are reacted with amines of the general formula (III)

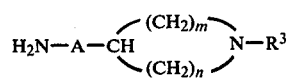
(III)

in which
A, $R^3$, m and n have the abovementioned meaning, optionally in the presence of inert organic solvents and an agent which splits off acid, at temperatures between $-20°$ and $110°$ C., or (b) 2-mercaptobenzamides of the general formula (IV)

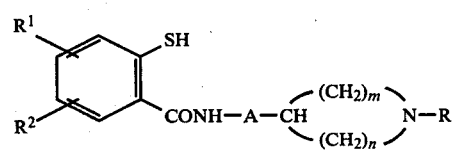
(IV)

in which
$R^1$, $R^2$, $r^3$, A, m and n have the abovementioned meaning, are reacted with equivalent amounts of benzisothiazol-3-ones of the formula (V)

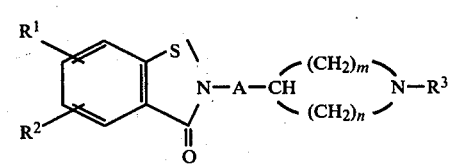
(V)

in which
$R^1$, $R^2$, $R^3$, A, m and n have the abovementioned meaning, optionally in the presence of inert organic solvents at temperatures between $-20°$ and $110°$ C.

It is surprising that the new diphenyl disulphide-2,2'-bis-carboxylic acid amides (I) have strong thrombocute aggregation inhibiting, thromboprophylactic and thrombolytic properties, since only hypoglycaemic and weakly biocidal properties, but no sort of antithrombotic properties, of the basic dithiosalicylic acid amines mentioned above as the state of the art have been disclosed. In this respect, the compounds according to the invention represent an enrichment of the art not only because of their novelty but also because of their novel application possibility.

If 5,5'-dichlorodiphenyl disulphide-2,2'-dicarboxylic acid chloride and 1-methylpiperidyl-4-aminomethane are used as the starting materials, the course of the reaction for process variant (a) can be represented by the following equation:

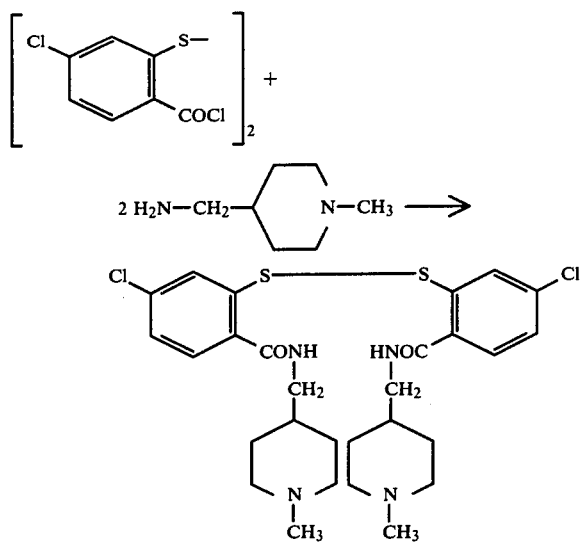

If 2-mercaptobenzoic acid (1-methylpiperidyl-3)-amide (see J. Het. Chem. 10, 381 (1973)) and 2-(1-methylpiperidyl-3)-1,2-benzisothiazol-3-one are used as the starting materials, the course of the reaction for process variant (b) can be represented by the following equation:

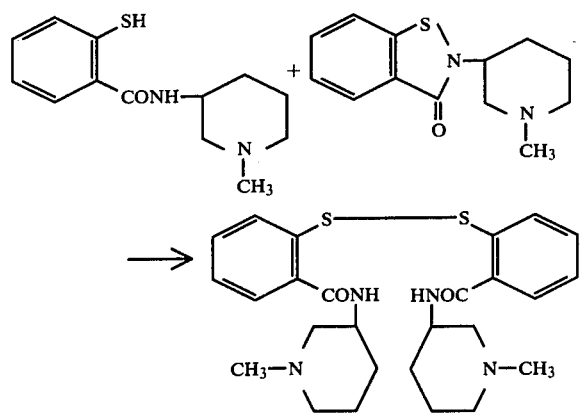

Process variant (a) is preferably carried out in the presence of inert organic solvents, such as alcohols, in particular alkanols having 1 to 4 carbon atoms, such as ethanol, isopropanol or butanol, ethers, in particular diethyl ether, tetrahydrofurane or dioxane, liquid hydrocarbons, in particular toluene, halogenohydrocarbons, in particular chloroform or carbon tetrachloride, or acetone, or methyl ethyl keton at temperatures between about −20° and 110° C., in particular between about 0° and 70° C.

Organic basis, such as amine compounds, in particular alkylamines having up to 8 carbon atoms and more particularly triethylamine, or inorganic basis, such as, for example, alkali metal carbonates or oxides or alkaline earth metal carbonates or oxides, can be used as agents which split off acid.

In general, the reaction is carried out under normal pressure, and optionally also under increased pressure.

Process variant (b) is preferably also carried out in the presence of the above mentioned inert organic solvents, such as alcohols, ethers, liquid hydrocarbons, halogenhydrocarbons or acetone and under the same temperature conditions as variant (a).

In the process of variant (b), a suitable organic or inorganic acid can be added, which then forms pharmaceutically acceptable acid addition salts with the basic compounds of the formula (I).

Examples of suitable acids which may be mentioned are: hydrochloric acid, sulphuric acid, phosphoric acid, hydrobromic acid, pamoric acid, fumaric acid, maleic acid, tartaric acid, citric acid, p-toluenesulphonic acid and naphthaline-1,5-disulphonic acid.

A resulting basic compound can be converted into a corresponding acid addition salt, for example by reacting it with an inorganic or organic acid, such as therapeutically useful acid, or with a corresponding anion exchange preparation, and isolating the desired salt. An acid addition salt may be converted into the free compound by treatment with a base, e.g. a metal hydroxide, ammonia or a hydroxyl ion exchange preparation. Therapeutically useful acids are, for example, inorganic acids, e.g. hydrochloric, hydrobromic, sulfuric, phosphoric, nitric or perchloric acid, or organic acids, e.g. carboxylic or sulfonic acids, such as formic, acetic, propionic, succinic, glycollic, lactic, lactic, malic, tartaric, citric, asorbic, maleic, hydroxymaleic, pyroracemic, phenylacetic, benzoic, 4-aminobenzoic, anthranilic, 4-hydroxybenzoic, salicyclic, aminosalicyclic, embonic, nicotinic, methanesulfonic, ethanesulfonic, hydroxy-ethanesulfonic, ethylenesulfonic, benzenesulfonic, halogenbenzenesulfonic, toluensulfonic, naphthalenesulfonic and sulfanilic acid; methionine, tryptophan, lysine and arginine.

These or other salts, for example, the picrates, can also be used for purification of the bases obtained; the bases are converted into salts, the salts are separated and the bases are liberated from the salts. In view of the close relationship between the free compounds and the compounds in the form of their salts, whenever a compound is referred to in this context, a corresponding salt is also intended, provided such is possible or appropriate under the circumstances.

Some of the diphenyl disulphide-dicarboxylic acid halides of the formula (II) which can be used according to the invention are known and can be prepared by known methods (J. Chem. Soc. (London) 1926, 921; and Ber. dtsch. chem. Ges. 31, 1,670 (1898)).

In the formula (II), $R^1$ preferably represents hydrogen, halogen, alkyl with 1 to 4 carbon atoms, alkoxy with 1 to 4 carbon atoms or aralkoxy, aryl preferably representing phenyl or naphthyl and the alkoxy group containing 1 to 4, in particular 1 or 2, carbon atoms, $R^2$ preferably represents hydrogen, halogen, especially chlorine or bromine, alkyl with 1 to 4 carbon atoms or alkoxy with 1 to 4 carbon atoms, or $R^1$ and $R^2$ together represent an alkylene or alkenylene chain with 2 to 5 carbon atoms, and X preferably represents chlorine or bromine.

The following diphenyl disulphide-dicarboxylic acid halides may be mentioned as examples: 5,5'-dibromo-diphenyl disulphide-2,2'-dicarboxylic acid chloride, 4,5,4',5'-tetrachloro-diphenyl disulphide-2,2'-dicarboxylic acid chloride, 3,5,3',5'-tetramethoxy-diphenyl disulphide-2,2'-dicarboxylic acid chloride, 5,5'-dimethyl-diphenyl disulphide-2,2'-dicarboxylic acid chloride, 4,5,4',5'-tetramethyl-diphenyl disulphide-2,2'-dicarboxylic acid chloride, 5,5'-diethyl-diphenyl disulphide-2,2'-dicarboxylic acid chloride, 5,5'-diethoxy-diphenyl disulphide-2,2'-dicarboxylic acid chloride, 5,5'- dibutoxy-diphenyl disulphide-2,2'-dicarboxylic acid chloride; 5,5'-dibenzyloxy-diphenyl disulphide-2,2'-dicarboxylic acid chloride and 4,5,4',5'-bis-tetramethylene-diphenyl disulphide-2,2'-dicarboxylic acid chloride.

Some of the amines of the general formula (III) which can be used according to the invention are known and can be prepared by known methods (J. Het. Chem. 10, 381 (1973); analogously to J. Med. Chem. 12, 949 (1969) and J. Het. Chem. 10, 381 (1973); analogously to DOS (German Published Specification) No. 2,506,515).

Examples which may be mentioned are: 1-ethyl-3-aminopiperidine, 1-isobutyl-3-amino-piperidine, 1-methyl-4-aminopiperidine, 1-propyl-4-amino-piperidine, 1-isobutyl-4-aminopiperidine, 1-methyl-piperidyl-3-aminomethane, 1-isopropylpiperidyl-3-aminomethane, 1-butyl-piperidyl-3-aminomethane, 1-isobutyl-piperidyl-4-aminomethane, 1-methyl-pyrrolidyl-2-aminomethane, 1-ethyl-pyrrolidyl-2-aminomethane and 1-methyl-2-aminomethyl-hexamethyleneimine.

In the formula (III), $R^3$ preferably represents alkyl with 1 to 4 carbon atoms, A preferably represents a single bond or an alkylene chain with 1 to 3 carbon atoms and m and n each represent a number from 0 to 5, m and n together having a value of 2 to 5.

The 2-mercaptobenzamides of the formula (IV) used as starting materials have not yet hitherto been disclosed but can be prepared in a known manner by reducing benzisothiazolinones of the formula (V) (analogously to J. Chem. Soc. (London) 1923, 3,313 and DOS (German Published Specification) No. 2,310,572) with metal hydrides, for example lithium aluminium hydride or sodium borohydride.

Examples which may be mentioned are: 2-mercapto-4,5-dichloro-N-(1-butylpiperidyl-3)-benzamide, 2-mercapto-4,6-dimethyl-N-(1-methyl-hexamethyleneimino-2)-methyl-benzamide, 2-mercapto-4,6-dimethoxy-N-(1-propylpiperidyl-4)-methyl-benzamide, 2-mercapto-4,5-tetramethylene-N-(1-ethylpyrrolidyl-2)-methyl-benzamide, 2-mercapto-4-butyl-N-(1-methylpiperidyl-4)-methyl-benzamide, 2-mercapto-4,6-dichloro-N-(1-ethylpiperidyl-3)-methyl-benzamide, 2-mercapto-4-isopropyl-N-(1-methylpiperidyl-4)-(ethyl-1)-benzamide and 2-mercapto-4-benzyloxy-N-(1-methyl-piperidyl-3)-methyl-benzamide.

The benzisothiazolinones of the formula (V) used as starting materials have not yet hitherto been disclosed, but can be prepared by known methods (German Reichspatent No. 1,147,947) by reacting phenylsulphenyl halides of the formula (VI)

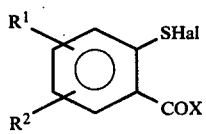

in which
 $R^1$ and $R^2$ have the meaning already mentioned,
 Hal represents chlorine or bromine and
 X denotes a leaving group, such as chlorine, bromine or alkoxy, with amines of the formula (III).

Examples which may be mentioned are: 2-(1-methylpyrrolidyl-3)-methyl-6-chloro-1,2-benzisothiazolin-3-one, 2-(1-methylpiperidyl-4)-(ethyl-1)-4,6-dimethyl-1,2-benzisothiazolin-3-one, 2-(1-isopropylpiperidyl-4)-methyl-4,6-dimethyl-1,2-benzisothiazolin-3-one, 2-(1-butylpiperidyl-4)-methyl-6-benzyloxy-1,2-benziso-thiazolin-3-one, 2-(1-methylhexamethyleneimino-2)-methyl-4,6-dimethyl-1,2-benzisothiazolin-3-one, 2-(1-methylpiperidyl-4)-methyl-6-ethoxy-1,2-benzisothiazolin-3-one, 2-(1-methylpiperidyl-4)-methyl-6-isopropyl-1,2-benziso-thiazolin-3-one, 2-(1-methylpiperidyl-4)-methyl-6-ethyl-1,2-benzisothiazolin-3-one, 2-(1-ethylpiperidyl-3)-6-bromo-1,2-benzisothiazolin-3-one, 2-(1-isobutylpiperidyl-3)-5,6-dichloro-1,2-benzisothiazolin-3-one, 2-(1-methylpiperidyl-3)-4,6-dimethyl-1,2-benzisothiazolin-3-one, 2-(1-propylpiperidyl-4)-6-chloro-1,2-benzisothiazolin-3-one, 2-(1-butylpiperidyl-4)-6-butoxy-1,2-benzisothiazolin-3-one and 2-(1-methylhexamethyleneimino-2)-methyl-6-bromo-1,2-benzisothiazolin-3-one.

Diphenyl disulphide-2,2'-bis-carboxylic acid amides of the formula (I) in which $R^1$ represents hydrogen, halogen, in particular chlorine or bromine, alkyl with 1 to 4 carbon atoms, alkoxy with 1 to 4 carbon atoms, phenalkoxy or naphthalkoxy, the alkoxy group containing 1 to 4, in particular 1 or 2, carbon atoms, $R^2$ represents hydrogen, halogen, especially chlorine or bromine, alkyl with 1 to 4 carbon atoms, alkoxy with 1 to 4 carbon atoms, or, together with the substituent $R^1$, forms an alkylene or alkenylene chain with 2 to 5 carbon atoms, $R^3$ represents alkyl with 1 to 4 carbon atoms, A represents a single bond or an alkylene chain with 1 to 4 carbon atoms and m and n each represent a number from 0 to 5, m and n together having a value of 2 to 5, are of particular importance.

In addition to the compounds mentioned in the examples of carrying out the invention, the following substances according to the invention are of particular interest: 5,5'-dimethyl-diphenyl disulphide-2,2'-dicarboxylic acid bis-N-(1-methyl-piperidyl-4)-methylamide, 3,3',5,5'-tetramethoxy-diphenyl disulphide-2,2'-dicarboxylic acid bis-N-(1-methylpiperidyl-4)-methylamide, 3,3',5,5'-tetramethoxy-diphenyl disulphide-2,2'-dicarboxylic acid bis-N-2-(1-methylpiperidyl-2)-ethyl-amide, 5,5'-diisopropyl-diphenyl disulphide-2,2'-dicarboxylic acid bis-N-(1-methyl-hexamethyleneimine-2)-methylamide, 5,5'-diisopropyl-diphenyl disulphide, 2,2'-dicarboxylic acid bis-N-(1-methyl-pyrrolidyl-2)-methylamide, 3,3',5,5'-tetrachloro-diphenyl disulphide-2,2'-dicarboxylic acid bis-N-(1-methyl-piperidyl-4)-methylamide, 3,3',5,5'-tetrachloro-diphenyl disulphide-2,2'-dicarboxylic acid bis-N-(1-methyl-pyrrolidyl-2)-methylamide, 3,3',5,5'-tetrachloro-diphenyl disulphide-2,2'-dicarboxylic acid bis-N-(1-methyl-hexamethyleneimine-2)-methylamide, 5,5'-dichloro-diphenyl disulphide-2,2'-dicarboxylic acid bis-N-(1-methyl-hexamethyleneimine-2)-methylamide, 4,5,4',5'-bis-tetramethylene-diphenyldisulphide-2,2'-dicarboxylic acid bis-N-(1-methyl-piperidyl-2)-methylamide, 4,5,4',5'-bis-tetramethylene-diphenyl disulphide-2,2'-dicarboxylic acid bis-N-(1-methyl-piperidyl-3)amide, 4,5,4',5'-bis-tetramethylene-diphenyl disulphide-2,2'-dicarboxylic acid bis-N-(1methyl-hexamethyleneimine-2)-methylamide, 5,5'-bis-benzyloxy-diphenyl disulphide-2,2'dicarboxylic acid bis-N-(1-methyl-piperidyl-4)-methylamide and 5,5'-bis-benzyloxy-diphenyl disulphide-2,2'-dicarboxylic acid bis-N-(1-methyl-pyrrolidyl-2)-methylamide.

The present invention includes a pharmaceutical composition containing as active ingredient a compound of the invention in admixture with a solid or liquefied gaseous diluent, or in admixture with a liquid diluent other than a solvent of a molecular weight less than 200 (preferably less than 350) except in the presence of a surface active agent.

The invention further provides a pharmaceutical composition containing as active ingredient a compound of the invention in the form of a sterile or isotonic aqueous solution.

The invention also provides a medicament in dosage unit form comprising a compound of the invention.

The invention also provides medicament in the form of tablets (including lozenges and granules), dragees, capsules, pills, ampoules or suppositories comprising a compound of the invention.

"Medicament" as used in this Specification means physically discrete coherent portions suitable for medical administration. "Medicament in dosage unit form" as used in this Specification means physically discrete coherent units suitable for medical administration each containing a daily dose or a multiple (up to four times) or sub-multiple (down to a fortieth) of a daily dose of the compound of the invention in association with a carrier and/or enclosed within an envelope. Whether the medicament contains a daily dose or, for example, a half, a third, or a quarter of a daily dose will depend on whether the medicament is to be administered once or, for example, twice, three times or four times a day respectively.

The diluents to be used in pharmaceutical compositions (e.g. granulates) adapted to be formed into tablets, dragees, capsules and pills include the following:

(a) fillers and extenders, e.g. starch, sugars, mannitol, and silicic acid; (b) binding agents, e.g. carboxymethyl cellulose and other cellulose derivatives, alginates, gelatine and polyvinyl pyrrolidone; (c) moisturizing agets, e.g. glycerol; (d) disintegrating agents, e.g. agar-agar, calcium carbonate and sodium bicarbonate; (e) agents for retarding dissolution e.g. paraffin; (f) resorption accelerators, e.g. quaternary ammonium compounds; (g) surface active agents, e.g. cetyl alcohol, glycerol monostearate; (h) adsorptive carriers, e.g. kaolin and bentonite; (i) lubricants, e.g. talc, calcium and magnesium stearate and solid polyethylene glycols.

The tablets, dragees, capsules and pills formed from the pharmaceutical compositions of the invention can have the customary coatings, envelopes and protective matrices, which may contain opacifiers. They can be so constituted that they release the active ingredient only or preferably in a particular part of the intestinal tract, possible over a period of time. The coatings, envelopes and protective matrices may be made, for example, of polymeric substances or waxes.

The ingredient can also be made up in microencapsulated form together with one or several of the above-mentioned diluents.

The diluents to be used in pharmaceutical compositions adapted to be formed into suppositories can, for example, be the usual water-soluble or water-insoluble diluents, such as polyethylene glycols and fats (e.g. cocoa oil and high esters [e.g. $C_{14}$-alcohol with $C_{16}$-fatty acid]) or mixtures of these diluents.

The pharmaceutical compositions which are powders and sprays can, for example, contain the usual diluents, e.g. lactose, talc, silicic acid, aluminium hydroxide, calcium silicate, and polyamide powder or mixtures of these substances. Aerosol sprays can, for example, contain the usual propellants, e.g. chlorofluorohydrocarbons.

The pharmaceutical compositions which are solutions and emulsions can, for example, contain the customary diluents (with, of course, the above-mentioned exclusion of solvents having a molecular weight below 200 except in the presence of a surface-active agent), such as solvents, dissolving agents and emulsifiers; specific examples of such diluents are water, ethyl alcohol, isopropyl alcohol, ethyl carbonate, ethyl acetate, benzyl alcohol, benzyl benzoate, propylene glycol, 1,3-butylene glycol, dimethylformamide, oils [for example ground nut oil], glycerol, tetrahydrofurfuryl alcohol, polyethylene glycols and fatty acid esters or sorbitol or mixtures thereof.

For parenteral adminstration, the solutions and emulsions should be sterile, and, if appropriate, blood-isotonic.

The pharmaceutical compositions which are suspensions can contain the usual diluents such as liquid diluents, e.g. water, ethyl alcohol, propylene glycol, surface-active agents (e.g. ethoxylated isostearyl alcohols, polyoxyethylene sorbite and sorbitane esters), microcrystalline, cellulose, aluminium metahydroxide, bentonite, agar-agar and tragacanth or mixtures thereof.

All the pharmaceutical compositions according to the invention can also contain colouring agents and preservatives as well as perfumes and flavouring additions (e.g. peppermint oil and eucalyptus oil) and sweetening agents (e.g. saccharin).

The pharmaceutical compositions according to the invention generally contain from 0.1 to 99.5, usually from 0.5 to 90% of the active ingredient by weight of the total composition.

In addition to a compound of the invention, the pharmaceutical compositions and medicaments according to the invention can also contain other pharmaceutically active compounds. They may also contain a plurality of compounds of the invention.

Any diluent in the medicaments of the present invention may be any of those mentioned above in relation to the pharmaceutical compositions of the present invention. Such medicaments may include solvents of molecular weight less than 200 as sole diluent.

The discrete coherent portions constituting the medicament according to the invention will generally be adapted by virtue of their shape or packaging, for medical administration and may be, for example, any of the following: tablets, (including lozenges and granulates) pills, dragees, capsules, suppositories and ampoules. Some of these forms may be made up for delayed release of the active ingredient. Some, such as capsules, include a protective envelope which renders the portions of the medicament physically discrete and coherent.

The preferred daily dose for administration of the medicaments of the invention is 0.5 mg to 10 g of active ingredient.

The production of the above-mentioned pharmaceutical compositions and medicaments is carried out by any method known in the art, for example, by mixing the active ingredient(s) with diluent(s) to form a pharmaceutical composition (e.g. a granulate) and then forming the composition into the medicament (e.g. tablets).

This invention further provides a method of combating (including prevention, relief and cure of) the above-mentioned diseases in human and non-human animals, which comprises administering to the animals a compound of the invention alone or in admixture with a diluent or in the form of a medicament according to the invention.

It is envisaged that these active compounds will be administered perorally, parenterally (for example intramuscularly, intraperitoneally or intravenously), or rectally preferably orally or parenterally. Preferred pharmaceutical compositions and medicaments are therefore those adapted for oral or parenteral administration.

In the case of parenteral use, the fact that the compounds according to the invention can be combined, in a suitable solvent, with an equivalent amount of a non-toxic inorganic or organic acid has proved particularly advantageous. Salts of this type can also have an increased importance for the oral use of the compounds according to the invention in that they accelerate or delay the resorption as desired.

In general it has proved advantageous, in the case of parenteral administration, to administer amounts of about 0.01, to 100 mg/kg. preferably about 0.1 to 10 mg/kg, of body weight daily to achieve effective results, whilst in the case of oral administration the dosage is about 0.1 to 100 mg/kg, preferably 1.0 to 50 mg/kg, of body weight daily.

Nevertheless it can at times be necessary to deviate from the amounts mentioned and in particular to do so as a function of the body weight of the test animal or of the nature of the administration route, but also because of the type of animal and its individual behavior towards the medicine or because of the nature of the formulation of the medicine and the time or interval at which it is administered. Thus it may be sufficient, in a few cases, to manage with less than the above-mentioned minimum amount, whilst in other cases the upper limit mentioned must be exceeded. Where larger amounts are administered it can be advisable to divide these into several individual administrations over the course of the day.

These statements apply to the use of the compounds according to the invention both in veterinary medicine and in human medicine.

The formulation may be illustrated by the following example:

500 g of 5,5'-dichloro-diphenyl disulphide-2,2' dicarboxylic acid bis-N-(1-methyl-piperidyl-4)-methylamide dihydrochloride are comminuted to a powder and mixed with 300 g of lactose and 200 g of potato starch and, after moistening with an aqueous gelatine solution, the mixture is granulated through a sieve. After drying, 60g of talc and 5 g of sodium lauryl-sulphate are added and the mixture is pressed to give 10,000 tablets with a content of active compound of 50 mg each.

PREPARATIVE EXAMPLES

EXAMPLE 1

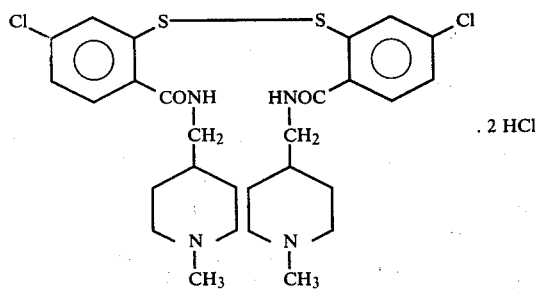

12.8 g of 1-methylpiperidyl-4-aminomethane, dissolved in 75 ml of alcohol, are added dropwise to a solution of 20.6 g of 5,5'-dichloro-diphenyl disulphide-2,2'-bis-carboxylic acid chloride in 75 ml of dry tetrahydrofurane at 0 – 10° C. After a few hours, the hydrochloride which has formed is filtered off and rinsed with a cold mixture of equal volumes of tetrahydrofurane and alcohol. After recrystallising twice from alcohol, 5.7 g of 5,5'-dichloro-diphenyl disulphide-2,2'-dicarboxylic acid bis-N-(1-methylpiperidyl-4)-methylamide dihydrochloride of melting point 195°–196° C. are obtained.

EXAMPLE 2

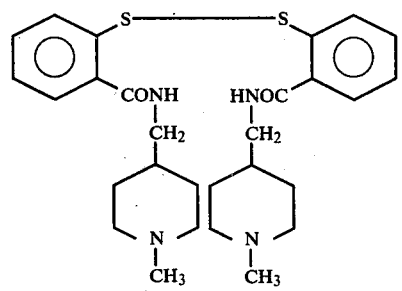

A toluene solution of 12.8 g of 1-methylpiperidyl-4-aminomethane are added dropwise to a solution of 17.2 g of diphenyl disulphide-2,2'-bis-carboxylic acid chloride in 75 ml of toluene, at 70° C., and the mixture stirred for 5 hours at 70° C. After cooling, the salt which has formed is filtered off and dissolved in water and the aqueous solution is clarified over animal charcoal and rendered alkaline with potassium carbonate. The reaction product is extracted with toluene/butanol 1:1, the organic phase is separated off, dried over sodium sulphate and evaporated and the evaporation residue is digested with acetone. After filtering off the solid, 11.5 g of diphenyl disulphide-2,2'-dicarboxylic acid bis-(1-methylpiperidyl-4)-methylamide of melting point 214°–215° C. are obtained.

EXAMPLE 3

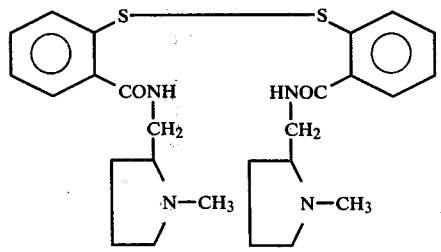

If diphenyl disulphide-2,2'-bis-carboxylic acid chloride is reacted with the equivalent amount of 1-methylpyrrolidyl-2-aminomethane instead of 1-methylpiperidyl-4-aminomethane, diphenyl disulphide-2,2'-dicarboxylic acid bis-(1-methylpyrrolidyl-2)-methylamide, which melts at 162°–163° C. when recrystallised from ethyl acetate, is obtained in a 42% yield in accordance with the procedure of Example 2 at a reaction temperature of 28° to 30° C.

EXAMPLE 4

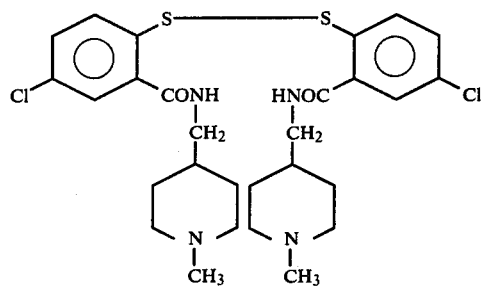

If 4,4'-dichloro-diphenyl disulphide-2,2'-bis-carboxylic acid chloride is reacted with the equivalent amount of 1-methyl-piperidyl-4-aminomethane in a tetrahydrofurane/ethanol mixture analogously to Example 1, 4,4'-dichloro-diphenyl disulphide-2,2'-dicarboxylic acid bis-N-(1-methylpiperidyl-4)-methylamide dihydrochloride, which melts at 233°-234° C. when converted into the base analogously to Example 2 and recrystallised from ethanol/ether, is obtained. Yield 25% of theory.

EXAMPLE 5

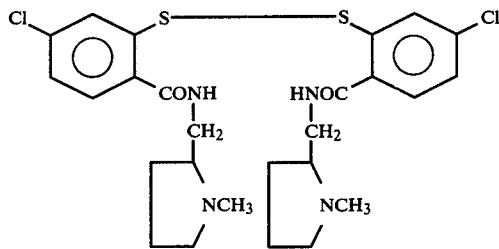

If 5,5'-dichloro-diphenyl disulphide-2,2'-bis-carboxylic acid chloride is reacted with the equivalent amount of 1-methyl-pyrrolidyl-2-aminomethane, 5,5'-dichloro-diphenyl disulphide-2,2'-dicarboxylic acid bis(1-methyl-pyrrolidyl-2)-methylamide, which melts at 200° C. when recrystallised from ethanol, is obtained in about 45% yield at a reaction temperature of 5°-10° C. in accordance with the procedure of Example 2. The hydrochloride of this compound melts at 140°-142°.

EXAMPLE 6 (Variant b)

1.75 g of sodium borohydride are introduced in portions into a solution of 11 g of 2-(1-methylpiperidyl-4)-methyl-6-chloro-1,2-benzisothiazol-3-one (melting point 144°-145° C.) in 135 ml of ethanol, the temperature being allowed to rise to 30° C. After several hours, the solution is rendered acid to Congo Red with concentrated hydrochloric acid, stirred for some time and filtered and the filtrate is concentrated in vacuo. A precipitate is obtained by addig sodium bicarbonate solution and is filtered off, dried in vacuo and recrystallised from dimethylformamide. Yield, after working up the crystallisation mother liquor, 9.9 g of 2-mercapto-4-chlorobenzoic acid (1-methylpiperidyl-4)-methyl amide of melting point 248°-249° C.

2.98 g of finely powdered 2-mercapto-4-chlorobenzoic acid (1-methylpiperidyl-4)-methylamide are rapidly introduced into a warm solution of 2.96 g of 2-(1-methylpiperidyl-4)-methyl-6-chloro-1,2-benzisothiazol-3-one in 15 ml of tetrahydrofurane and 10 ml of ethanol and the mixture is warmed externally to 50° C. for some time. After cooling, the 5,5'-dichloro-diphenyl disulphide-2,2'-dicarboxylic acid bis-N-(1-methylpiperidyl-4)-methylamide (base of Example 1) which has formed is filtered off, digested with a little acetone, filtered off again and dried. Yield 5.2 g of melting point 234°-235° C.

EXAMPLE 7

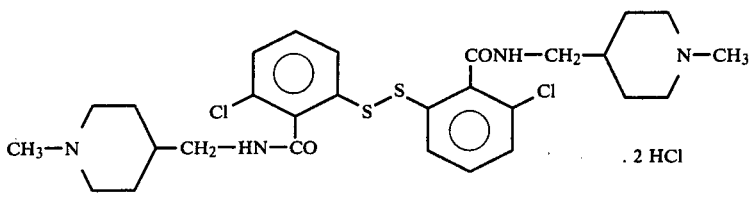

Analogously to Example 1, 3,3'-dichloro-diphenyl disulphide-2,2'-bis-carboxylic acid chloride and 1-methylpiperidyl-4-aminomethane gives 3,3'-dichloro-diphenyl disulphide-2,2'-bis-N-(1-methylpiperidyl-4)-methylamide, the hydrochloride of which forms colourless prisms of melting point 280° C. after recrystallisation from 90% strength alcohol. Yield 30% of theory.

EXAMPLE 8

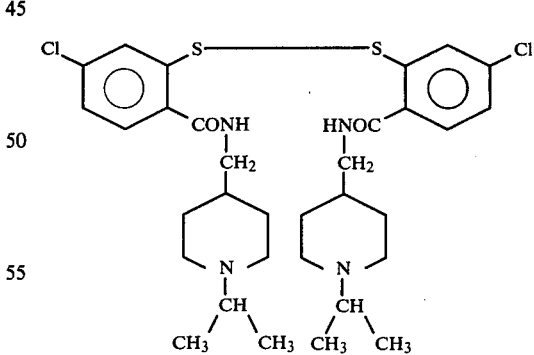

Analogously to Example 6, equivalent amounts of 2-(1-isopropylpiperidyl-4)-methyl-6-chloro-1,2-benzisothiazolinone-3 (see our copending application No. 2525/77 (Case Le A 16890) Example 36, m.p. 134°-135° from acetone), and 2-mercapto-4-chlorobenzoic acid-(1-isopropylpiperidyl-4)-methylamide (melting point 242°-243°) in a mixture of THF and ethanol, give 5,5'-dichloro diphenyldisulphide-2,2'-dicarboxylic acid-bis-N-(1-isopropylpiperidyl-4)-methylamide of melting point 216-217 from ethanol.

EXAMPLE 9

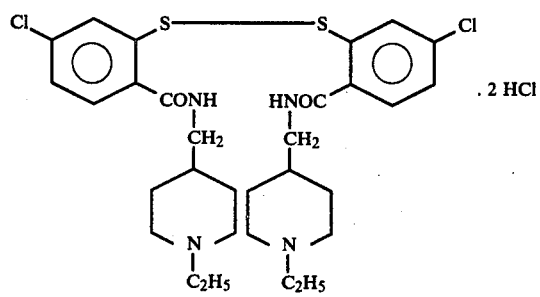

Analogously to Example 1, 5,5'-dichlorodiphenyl disulphide-2,2'-bis-carboxylic acid chloride and 1-ethyl-piperidyl-4-amino methane (boiling point $_{15}$ 90°–92° prepared analogously to T. Singh et al. J. Med. Chem. 12, 949 (1969) and L. M. Werbel et al from 4-acetylaminomethyl-pyridine and ethylchloride) give 5,5'-dichloro-diphenyl disulphide-2,2'-dicarboxylic acid-bis-N-(1-ethylpiperidyl-4)-methyl-amide-dihydrochloride of melting point 238°–240° after crystallisation. The crystallisation is from methanol acetone.

J. Het. Chem. 10, 381(1973).

EXAMPLE 10

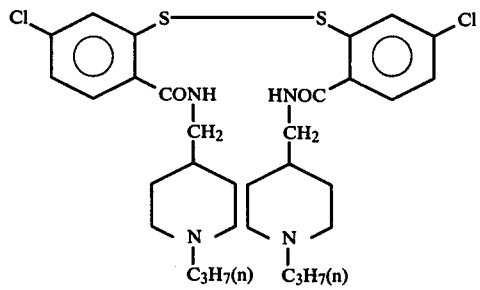

Analogously to Example 1 5,5'-dichlorodiphenyl disulphide-2,2-bis-carboxylic acid chloride and 1-(n)-propylpiperidyl-4-amino methane (boiling point $_{15}$ 103°–104° prepared analogously to T. Singh et al. J. Med. Chem. 12, 949 (1969) and L. M. Werbel et al. J. Het. Chem. 10, 381 (1973) from 4-acetylaminomethyl-pyridine and propylchloride) give 5,5'-dichloro-diphenyl disulphide-2,2'-dicarbocyclic acid-bis-N-(1-(n)-propylpiperidyl-4)-methylamide-dihydrochloride of melting point 173°–175°. The crystallisation is from ethanol/acetone.

What is claimed is:

1. A diphenyl disulphide-2,2'-bis-carboxylic acid amide of the general formula (I)

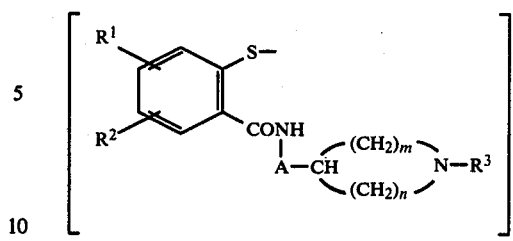

in which
  $R^1$ represents hydrogen, halogen, alkyl with 1 to 4 carbon atoms, alkoxy with 1 to 4 carbon atoms, phenalkoxy or naphthalkoxy, the alkoxy group containing 1 to 4 carbon atoms,
  $R^2$ represents hydrogen, halogen, alkyl with 1 to 4 carbon atoms, alkoxy with 1 to 4 carbon atoms or, together with the substituent $R^1$, forms an alkylene or alkenylene chain with 2 to 5 carbon atoms,
  $R^3$ represents alkyl with 1 to 4 carbon atoms,
  A represents a single bond or an alkylene chain with 1 to 3 carbon atoms and
  m and n each represent 0 or an integer of from 1 to 5, m and n together having a value of from 2 to 5, or an acid addition salt thereof.

2. A pharmaceutical composition containing as an active ingredient a thromboembolic effective amount of a compound according to claim 1 in admixture with a solid or liquefied gaseous diluent or in admixture with a liquid diluent other than a solvent of a molecular weight less than 200 except in the presence of surface-active agent.

3. A pharmaceutical compositon containing as an active ingredient a therombolic effective amount of a compound according to claim 1 in the form of a sterile or isotonic aqueous solution.

4. A composition according to claim 2 containing from about 0.5 to 95% by weight of the said active ingredient.

5. A composition according to claim 3 containing from about 0.5 to 95% by weight of the acid active ingredient.

6. A medicament in dosage unit form comprising a thromboembolic effective amount of a compound according to claim 1 and an inert pharmaceutical carrier.

7. A medicament of claim 6 in the form of tablets, pills, dragees, capsules, ampoules, or suppositories.

8. A method of combating thromboembolic illness in warm-blooded animals which comprises administering to the said animals, thromboembolic effective amount of an active compound according to claim 1 either alone or in admixture with a diluent or in the form of a medicament.

9. A method according to claim 8 in which the active compound is administered in an amount of 0.01 to 100 mg per kg body weight per day.

10. A method according to claim 8 in which the active compound is administered orally or parenterally.

* * * * *

UNITED STATES PATENT AND TRADEMARK OFFICE
CERTIFICATE OF CORRECTION

PATENT NO. : 4,153,702
DATED : May 8, 1979
INVENTOR(S) : Ulrich Hörlein, et al.

It is certified that error appears in the above-identified patent and that said Letters Patent are hereby corrected as shown below:

Column 1, line 57-58, delete "thrombolic" before "1"
Column 2, line 53, "thrombocute" should be
   --thrombocyte--.
Column 2, line 58, "amines" should be --amides--.

Column 6, line 57, "3)amide" should be --3)-amide--.
Column 7, line 33, "agets" should be --agents--.
Column 7, line 48, "possible" should be --possibly--.
Column 11, line 18, "ofl" should be --of 1--.
Column 11, line 52, "bis(1-" should be --bis-(1- --.
Column 11, line 68, "addig" should be --adding--.

UNITED STATES PATENT AND TRADEMARK OFFICE
CERTIFICATE OF CORRECTION

PATENT NO. : 4,153,702  Page 2 of 2
DATED : May 8, 1979
INVENTOR(S) : Ulrich Hörlein, et al.

It is certified that error appears in the above-identified patent and that said Letters Patent are hereby corrected as shown below:

Column 13, line 28 delete "J. Het. Chem. 10,381 (1973.".

Column 14, line 28 insert "-" after "thrombo".

Column 14, line 35 "therombolic" should be --thrombo-embolic--.

Column 14, line 45 insert "-" after "thrombo".

Column 14, line 49, insert "-" after "thrombo".

Signed and Sealed this

Sixth Day of November 1979

[SEAL]

Attest:

RUTH C. MASON
Attesting Officer

LUTRELLE F. PARKER
Acting Commissioner of Patents and Trademarks